United States Patent [19]

Martin

[11] Patent Number: 5,188,593

[45] Date of Patent: Feb. 23, 1993

[54] DUAL LUMEN CATHETER

[75] Inventor: Geoffrey S. Martin, Mississauga, Canada

[73] Assignee: Vas-Cath Incorporated, Mississauga, Canada

[21] Appl. No.: 742,071

[22] Filed: Aug. 7, 1991

Related U.S. Application Data

[60] Continuation of Ser. No. 543,692, Jun. 26, 1990, Pat. No. 5,057,073, which is a division of Ser. No. 184,529, Apr. 21, 1988, Pat. No. 4,961,809.

[51] Int. Cl.$^5$ .............................................. A61M 3/00
[52] U.S. Cl. ...................................... 604/43; 604/280
[58] Field of Search ................... 604/43, 44, 45, 280, 604/281, 284, 164

[56] References Cited

U.S. PATENT DOCUMENTS

| | | | |
|---|---|---|---|
| 3,485,234 | 12/1969 | Stevens | 604/281 |
| 4,149,535 | 4/1979 | Volder | 604/43 |
| 4,385,631 | 5/1983 | Uthmann | 604/284 |
| 4,403,983 | 9/1983 | Edelman | 604/43 |
| 4,568,329 | 2/1986 | Mahurkar | 604/43 |
| 4,619,643 | 10/1986 | Bai | 604/43 |
| 5,057,073 | 10/1991 | Martin | 604/43 |

Primary Examiner—John D. Yasko
Attorney, Agent, or Firm—Rogers & Scott

[57] ABSTRACT

A dual lumen catheter, for insertion into a vein of a patient for use in haemodialysis treatments, having first and second portions defining a shorter intake lumen and a longer return lumen. The intake lumen is closed at its end and receives blood through at least one opening in the side wall of the catheter and the second lumen includes the second portion which is of smaller cross-section than the first portion. Also described is a catheter having an intake lumen and a return lumen in which the return lumen has a tip of different stiffness from the main body of the catheter, the intake lumen being closed at its end and receiving fluid through an opening in the side wall of the catheter.

8 Claims, 8 Drawing Sheets

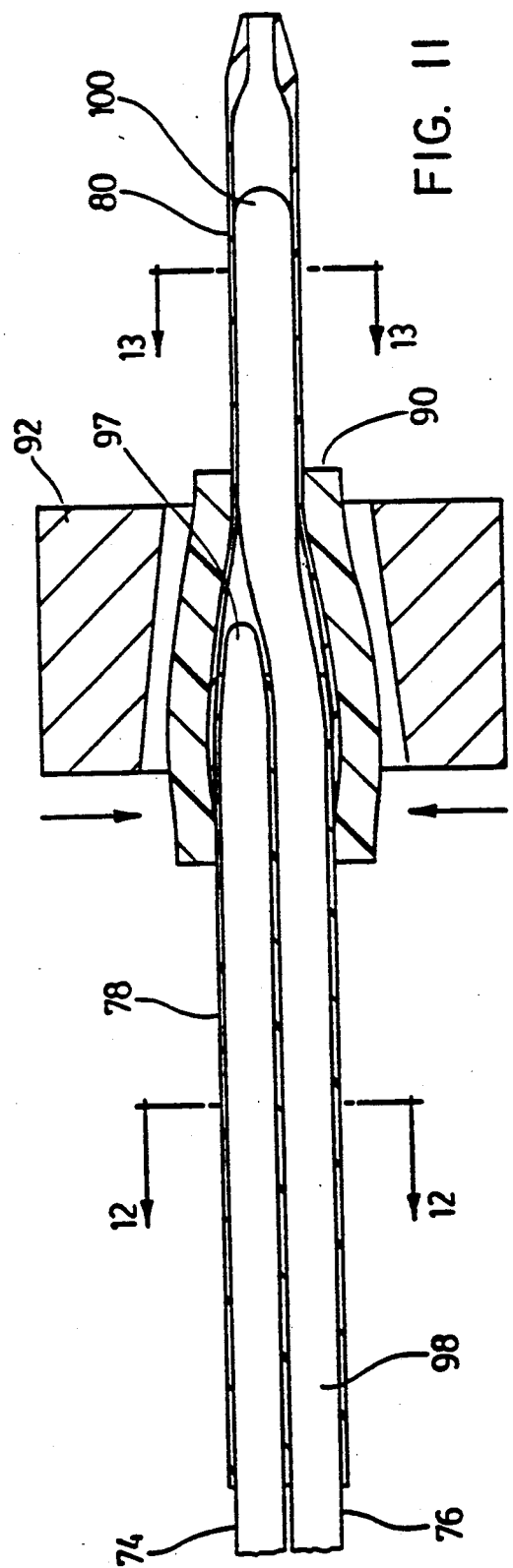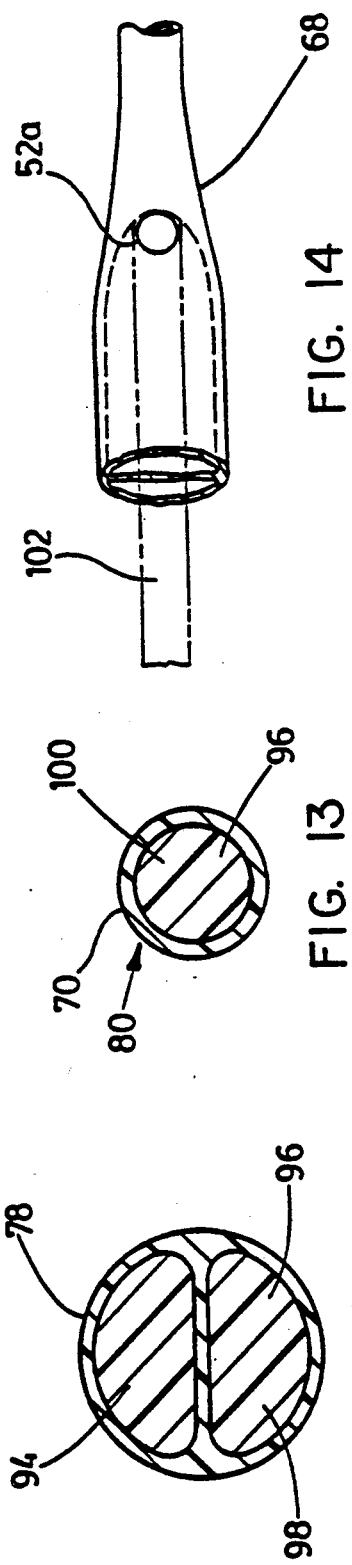

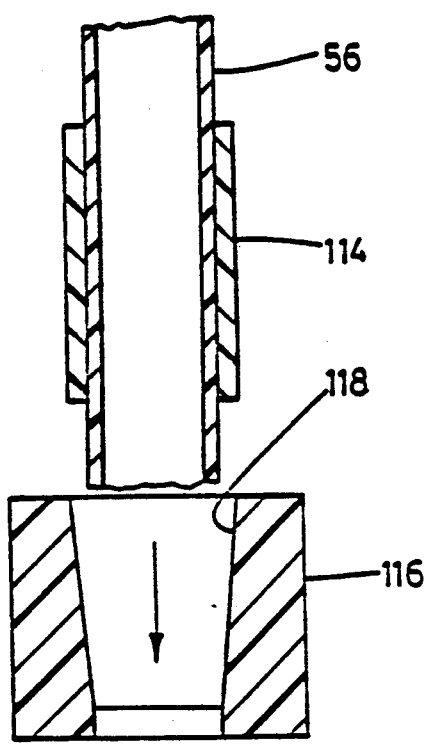
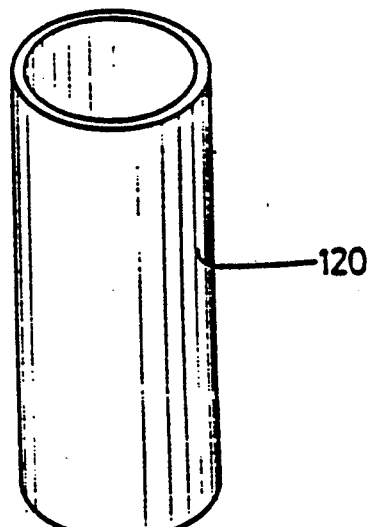
FIG. 17
FIG. 18

DUAL LUMEN CATHETER

This application is a continuation of application Ser. No. 07/543,692 filed on Jun. 26, 1990 now U.S. Pat. No. 5,057,073, which was a divisional application of application Ser. No. 07/184,529 filed on Apr. 21, 1988 now U.S. Pat. No. 4,961,809.

This invention relates to a dual lumen catheter and more particularly to such a catheter for insertion into a vein of a patient for use in haemodialysis treatments.

Dual lumen catheters have been available for many years for a variety of medical purposes. It is only in recent years, however, that such catheters have been developed for use in haemodialysis. The general form of dual lumen catheters goes back to as early as 1882 when Pfarre patented such a catheter in the United States under Ser. No. 256,590. This patent teaches a flexible dual lumen catheter which is used primarily for cleaning and drainage of, for example, the bladdar, rectum, stomach and ear. In this type of catheterization, the catheter is introduced into an existing body orifice without the use of any puncturing needle or guidewire.

More recently, a catheter was developed and patented by Blake et al under U.S. Pat. No. 3,634,924. This 1972 patent teaches a double lumen cardiac balloon catheter which is introduced into a large vein and the balloon inflated to control the flow in the vein. The catheter can in fact be placed by using the balloon as a "sail" to move with the blood from an ante-cubital or other peripheral vein through for example, the right heart chambers into the smaller radicals of the pulmonary artery where the catheter takes up its intended function. This patent is particularly interesting because it teaches the use of two lumens in a single body and explains how to make a tip for a dual lumen structure of the type which has become common for a variety of purposes including haemodialysis. The structure uses a plug to seal the end of one lumen and a wire which retains the shape of the other lumen during formation of the tip in a heated die.

Further patents which teach dual lumen catheters for general use include the following U.S. Pat. Nos.: 701,075; 2,175,726; 2,819,718; 4,072,146; 4,098,275; 4,134,402; 4,406,656 and 4,180,068.

Vascular catheter access by surgical cut-down techniques has been known to the medical profession for many years and, in fact, can be traced back to the 17th century. However, it was only with the introduction of the Seldinger technique in 1953 or thereabouts that new approach could be used to improve vascular access. This technique was taught in an article published by Dr. Sven Ivar Seldinger resulting from a presentation made at the Congress of the Northern Association of Medical Radiology at Helsinki in June of 1952. The technique essentially involves the use of a hollow needle to make an initial puncture, and a wire is then entered through the needle and positioned in the vessel. The needle is withdrawn and the catheter is entered percutaneously over the wire which is itself later withdrawn. With this technique it became possible to make less traumatic vascular access and this has now become the accepted method of performing access in numerous medical techniques. One of these techniques which has been the subject of much research and development is haemodialysis.

Haemodialysis can be defined as the temporary removal of blood from a patient for the purpose of extracting or separating toxins therefrom and the return of the cleaned blood to the same patient. Haemodialysis is indicated in patients where renal impairment or failure exists, that is, in cases where the blood is not being properly or sufficiently cleansed, (particularly to remove water) by the kidneys.

In the case of chronic renal impairment or failure, haemodialysis has to be carried out on a repetitive basis. For example, in end stage kidney disease where transplanation of kidneys is not possible or for medical reasons is contra-indicated, the patient will have to be dialysed about 100 to 150 times per year. This can result in several thousand accesses to the blood stream to enable the active haemodialysis to be performed over the remaining life of the patient.

Towards the end of 1960, Dr. Stanley Shaldon and colleagues developed, in the Royal Free Hospital in London, England, a technique for haemodialysis by percutaneous catherization of deep blood vessels, specifically the femoral artery and vein. The technique was described in an article published by Dr. Shaldon and his associates in the Oct. 14th, 1961 edition of at Pages 857 to 859. Dr. Shaldon and his associates developed single lumen catheters having tapered tips for entry over a Seldinger wire to be used in haemodialysis. Subsequently, Dr. Shaldon and his colleagues began to insert single lumen inlet and outlet catheters in the femoral vein and this was reported in the British Medical Journal of Jun. 19th, 1963. The purpose of providing both inlet and outlet catheters in the femoral vein was to explore the possibility of a "self-service" approach to dialysis. Dr. Shaldon was subsequently successful in doing this and patients were able to operate reasonably normally while carrying implanted catheters which could be connected to haemodialysis equipment periodically.

Some use was made of a flexible dual lumen catheter inserted by surgical cut-down as early as 1959. An example of such a catheter is that of McIntosh and colleagues which is described in the Journal of the American Medical Association of Feb. 21, 1959 at pages 137 to 138. In this publication, a form of dual lumen catheter is made of non-toxic vinyl plastic and described as being inserted by cut-down technique into the saphenous vein to the inferior vena cava.

The advantage of dual lumen catheters in haemodialysis is that only one vein access need be affected to establish continued dialysis of the blood, because one lumen serves as the conduit for blood flowing from the patient to the dialysis unit and the other lumen serves as a conduit for treated blood returning from the dialysis unit to the patient. This contrasts with prior systems where either two insertions were necessary to place the two catheters as was done by Dr. Shaldon, or a single catheter was used with a complicated dialysis machine which alternately removed blood and returned cleansed blood.

The success of Dr. Shaldon in placing catheters which will remain in place for periodic haemodialysis caused further work to be done with different sites. Dr. Shaldon used the femoral vein and in about 1977 Dr. P. R. Uldall, in Toronto Western Hospital, Canada, began clinical testing of a subclavian catheter that would remain in place between dialysis treatments. An article describing this was published by Dr. Uldall and others in Dialysis and Transplantation, Volume 8, No. 10, in October 1979. Subsequently Dr. Uldall began experimenting with a coaxial dual lumen catheter for subclavian insertion and this resulted in Canadian Pat. No. 1,092,927 which issued on Jan. 6, 1981. Although this particular form of catheter has not achieved significant success in the marketplace, it was the forerunner of dual lumen catheters implanted in the subclavian vein for periodic haemodialysis.

The next significant step in the development of a dual lumen catheter for haemodialysis is Canadian Pat. No. 1,150,122 to Martin who produced a catheter which achieved some commerical success. The catheter avoided the disadvantages of the Uldall structure.

A subsequent development is shown in U.S. Pat. No. 4,451,252 also to Martin. This utilizes the well known dual lumen configuration in which the lumens are arranged side-by-side separated by a diametric septum. The structure shown in this patent provides for a tip making it possible to enter a Seldinger wire through one of the lumens and to use this wire as a guide for inserting the catheter percutaneously. This type of structure is shown in a European Patent Application to Edelman published under No. 0 079 719, and in U.S. Pat. Nos. 4,619,643, 4,583,968, 4,568,329, 4,543,087, 4,692,141, 4,568,329, and U.S. Pat. No. Des. 272,651.

To insert a catheter over a guide wire using the Seldinger technique, or indeed any similar technique, the tip of the catheter must possess sufficient rigidity so that it does not concertina as it contacts the skin because this would enlarge the skin puncture as the catheter is being entered over the wire. To some extent this is at odds with the desirable material qualities of the main body of catheter which should be soft and flexible for patient comfort. In an effort to solve this problem, manufacturers have formed a variety of tips within the limitations of using a single extrusion from which the body and tip are formed. The result is that the tips have in general been made by using some of the excess material found in the shorter intake lumen. This has led to other problems such as very stiff tips which are unsuitable for prolonged placement in a vein; voids which can accumulate stagnant blood; and short stubby tips which are less desirable for insertion than longer more gradual tips. Also, because there is not always sufficent material to form the tip, plugs have been added with a varying degree of success because if the plug is not placed accurately the resulting structure may have unacceptable spaces where blood can stagnate.

It must also be recognized that the degree of rigidity in the tip becomes more important if the catheter is to reside in the patient for prolonged periods, as is becoming more common in many treatments, notably haemodialysis. This is because although ideally the catheter lies in the middle of the vein, in practice it will bear against the vessel wall. In such circumstances it is possible that a stiff tip could damage or even embed itself in the vessel wall when left in place for extended periods.

In summary there are a number of desirable features for a catheter of the type to be used in procedures where the catheter is to remain in the patient between treatments. Firstly, the body of the catheter should be flexible to take up curved positions with a minimum of stress. Secondly, after insertion the tip should take up position in the vein without placing a load on the vein wall, and thirdly the catheter must be sufficiently robust to withstand the forces applied during insertion using the Seldinger technique. Also, the external surface of the catheter should be smooth and any changes in cross-sectional area along the length of the catheter should take place gradually and without sudden changes in section. It is among the objects of this invention to provide catheters which meet some or all of these desirable characteristics and to provide methods of making such catheters.

In one of its aspects, the invention provides a dual lumen catheter having first and second portions defining a shorter intake lumen and a longer return lumen. The intake lumen is closed at its end and receives fluid through at least one blood intake aperture in the side wall of the catheter and the second lumen includes the second portion which is of smaller cross-section than the first portion and includes at least one blood return aperture in the second lumen on the same side of the catheter as the blood intake aperture.

This and other aspects of the present invention will now be described in more detail, by way of example, with reference to the accompanying drawings, in which:

FIGS. 9 to 14 are sectional views showing the various steps in the manufacture of the distal end of the catheter as shown in FIG. 3;

FIGS. 17 to 21 are diagrammatic perspective views of one end of the catheter showing the steps in the manufacture of the Y-shaped branching connector and associated parts.

The invention will be described in detail with reference to a preferred embodiment to be used for haemodialysis. However the drawings are exemplary of the invention and unless otherwise stated, are not intended to be limited by the restraints of size and properties created by haemodialysis procedures.

Figure 1:
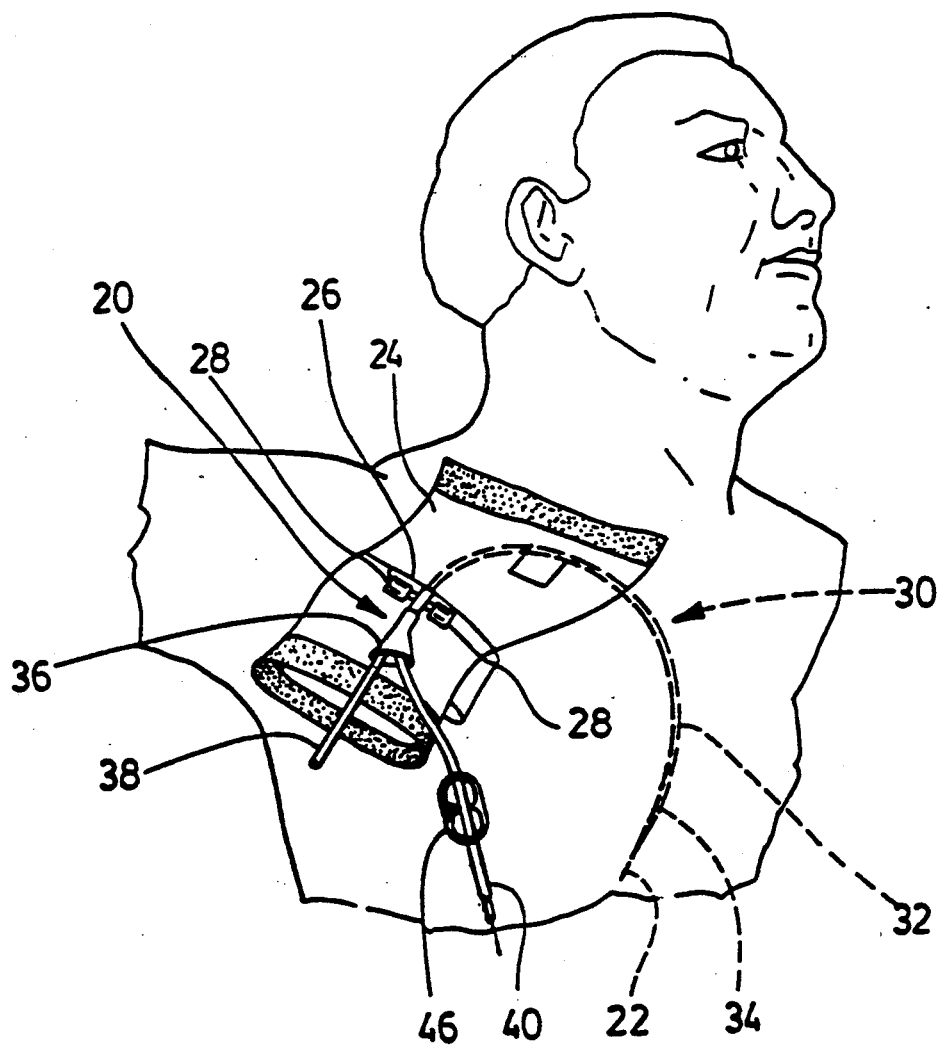
FIG. 1 is a diagrammatic view of a dual lumen catheter according to a preferred embodiment of the present invention, inserted in the subclavian vien of a patient.

Reference is made first to FIG. 1 of the drawings which illustrates a dual lumen catheter indicated generally by reference numeral 20 according to a preferred embodiment of the present invention, and a patient shown, by way of example, receiving the catheter in the subclavian vein using a Seldinger wire 22. The catheter 20 is to be used for haemodialysis treatment and could of course be entered in a similar manner in the femoral vein.

The catheter 20 is secured to a conventional dressing 24 by an attachment fitting 26 having wing tabs 28, and the dressing 24, in turn, is secured to the skin of the patient. As shown, the catheter passes through the dressing 24 and, as can be seen in broken outline, a flexible elongate and substantially cylindrical body 30, formed of polyurethane extrusions (as will be described below) is inserted through the skin and into the subclavian vein in the downstream direction. The catheter 20 has at its distal end 32 a tip 34, decribed in greater detail below. At the other end of the body 30 is a generally Y-shaped branching connector 36, which protrudes outwardly and is secured by dressing 24. Cylindrical blood extraction and return tubes 38, 40 are attached to the connector 36, a more detailed description of which is also provided below. For the moment it is sufficient to state that these tubes 38, 40 are connected to lumens running through the body 30.

Figure 2:
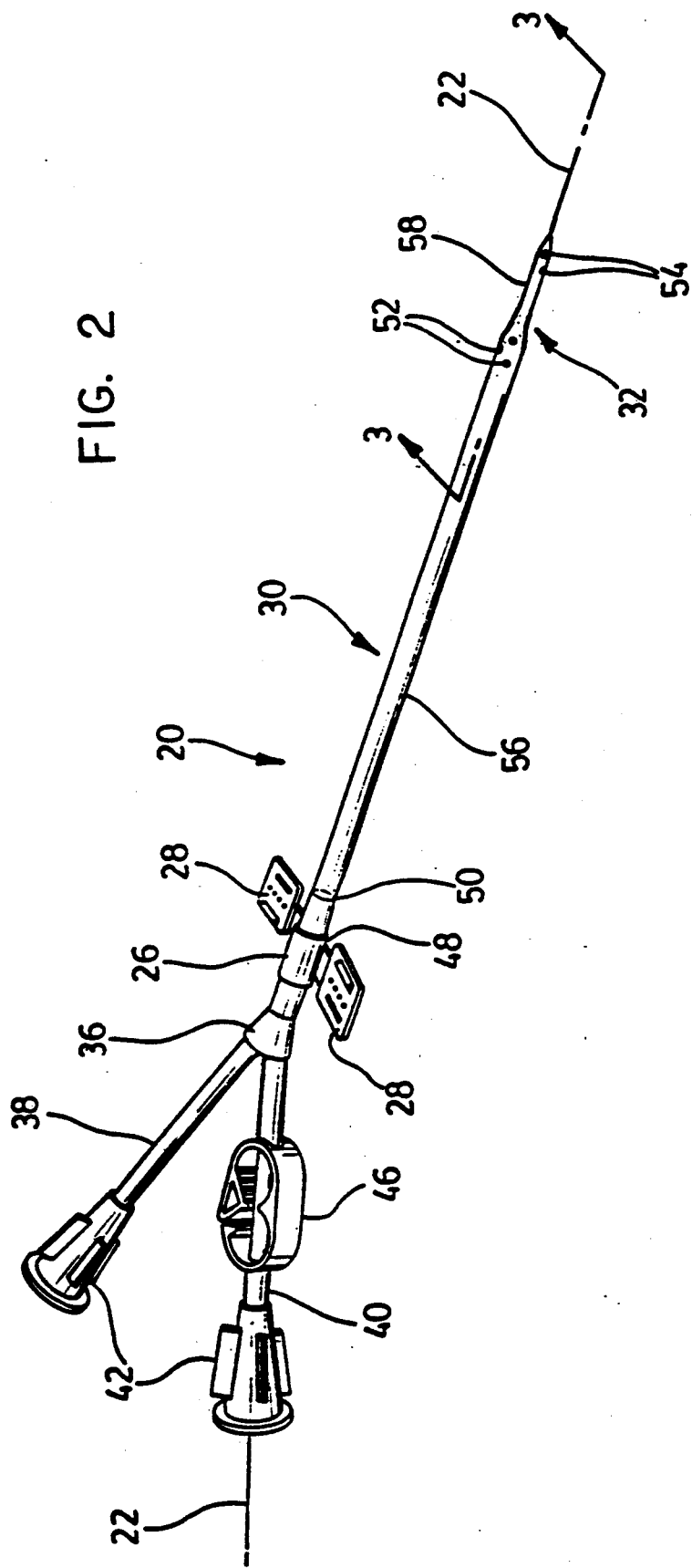
FIG. 2 is a diagrammatic perspective view of the catheter of FIG. 1 drawn to a larger scale.

FIG. 2 shows the catheter 20 in greater detail. The body 30 terminates at its proximal end in the connector 36, for receiving the blood extraction and return tubes 38, 40. These tubes terminate at their outer ends at respective female luer fittings 42 for connection to complementary male luer fittings (not shown) leading to a dialysis machine, and carry closure clamps 46 (one of which is shown) to selectively close the tubes.

The wing tabs 28, sometimes known as suture wings, are formed integrally with a central tubular portion 48 which can rotate on the body 30 and is retained in place by a shoulder on the end of the connector 36 and a second shoulder on a reinforcing portion 50 so that the catheter 20 can be rotated relative to the tabs 28. This rotation is sometimes necessary after insertion of the catheter 20 to change the position of intake side apertures in the distal end 32 if the apertures happen to be occluded by engagement of the wall of the vein. Details of the apertures are provided below.

As will be described, the reinforcing portion 50 is blended into the body 30 over the length of the portion and assists in strengthening the catheter to minimize the likelihood of kinking. Also, the portion 50 assists in sealing the puncture site where the catheter enters the patient.

As will be described with reference to subsequent views, the return tube 40 is aligned with a return lumen to permit the Seldinger wire 22 to pass through the catheter. The wire exits at the tip 34 which is of a reduced cross-section so that the catheter can slide over the wire and into the patient. The extraction and return tubes 38, 40 are linked at the connector 36 with lumens in the body 30 to connect with respective groups of apertures 52, 54 (some of which can be seen in this view) at the distal end of the catheter. As a result, when inserted and in use, blood can be removed and returned in a closed loop with a haemodialysis machine using the tubes 38, 40. It should be noted that one of the apertures 54 is on the same side of the catheter as apertures 52 so that blood returning through aperture 54 will tend to cause a reaction with the vein wall to hold the catheter off the wall and hence to keep apertures 52 away from the wall to avoid occlusion of apertures 52 by the vein wall.

As seen in FIG. 2, the body 30 is made up of a main or first portion 56 and a lesser second portion 58 at the distal end of the first portion.

Figures 3, 4, 5, 6, 7:
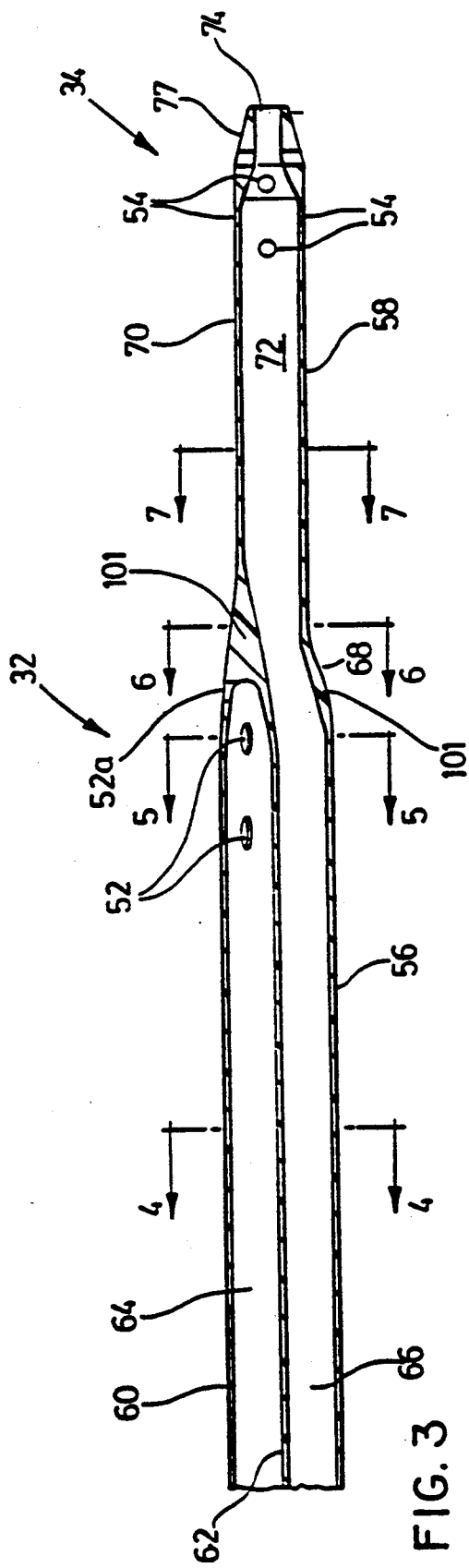
FIG. 3 is a sectional view on line 3—3 of FIG. 2 drawn to a larger scale and showing details of the structure of the distal end of the catheter.
FIGS. 4 to 7 are sectional views taken on the corresponding lines of section of FIG. 3, and showing complete sections.

Turning now to FIG. 3 of the drawings it will be seen that the distal end 32 is made up of the distal end of the first portion 56 and the second portion 58. The portion 56 has an outer wall 60 and an integral septum 62 extending diametrically to define two D-shaped passageways 64, 66 (see also FIG. 4) having rounded corner portions to avoid blood stagnation. The passageway 64 is closed at its distal end to define an extraction lumen and the passageway 66 connects with the second portion 58 to define a return lumen.

The first and second portions 56, 58 merge smoothly at a transition portion 68 of decreasing cross-section and the second portion leads smoothly from the first portion 56. The tubular second portion 58 comprises an outer wall 70 which combines with passageway 66 to form a return lumen 72. The extraction lumen consists essentially of the passageway 64 and terminates in the transition portion 68 of decreasing cross-section where the septum 62 merges with the outer wall 60. The distal end of the extraction lumen is formed by material at the transition portion 68 such that one of the openings 52a is at the very end of the lumen to minimize the risk of blood stagnating at the end of the lumen.

The other apertures 52 are provided at spaced points in the outer wall 60, thus allowing the inflow of blood from the vein into the lumen. The return apertures 54 are located at spaced points in the outer wall 70 of the second portion 58. The tip 34 also includes an end aperture 74 through which the Seldinger wire 22 passes. The end aperture 74 is of corresponding diameter to the Seldinger wire 22.

As will be noted from FIG. 3, in addition to the transition portion 68 between the first and second portions 56, 58, the tip 34 includes a portion of decreasing cross-section 77. Both of these portions 68, 77 facilitate insertion of the catheter 20 over the Seldinger wire 22 at the puncture site as the increase in cross-section from the tip 34 to the first portion 56 is gradual and the second portion 58 acts as a dilator for the larger first portion 56. The gradual increase in cross-section also reduces the likelihood of kinking at the points on the catheter where the changes in cross-section occur.

As seen in the sectional and enlarged views 4 through 7, the cross-section of the catheter changes. FIG. 4 is a cross-section of the first portion 56 and shows the septum 62 extending diametrically to define the two similar D-shaped passageways 64 and 66 contained by the outer wall 60.

The section illustrated by FIG. 5 shows the initial stages of transition from the first portion 56 to the second portion 58. The passageway 64 is smaller and is converging towards its end. FIG. 6 shows the shape of lumen 72 during transition and it will be seen that there is some flatness at the top (as drawn) of the lumen 72 caused by the transition from D-shaped to round. Finally the section becomes round as shown in FIG. 7 with an outer diameter smaller than that of the portion 56 and also smaller than the transition diameter shown in FIG. 6.

When placed in a blood vessel the tip 34 of the catheter 20 will often rest against the side wall of the vessel. Where the catheter tip is of a stiff material the continued pressure of the tip against the vessel wall may be sufficient to damage the vessel wall or to embed the tip in the vessel wall. To obviate this problem, the first and second portions 56, 58 may be of material having different properties which are capable of assembly as will be described. For instance, the first portion 56 may be of a stiffer material than the second portion 58. It is also necessary that the catheter is not of a material that is so flexible that it will concertina as it is pushed over the Seldinger wire 22 during insertion at the puncture site. However, if only the tip or a short length of the distal end or of the catheter is more flexible or is of a more flexible material, and the remainder of the catheter is of a stiffer, but still flexible material, this concertina effect can be avoided.

The formation of the distal end of the catheter will now be described with reference to FIGS. 8 to 14, followed by a description of an alternative embodiment and the description of the formation of the connector 36.

Figure 8:
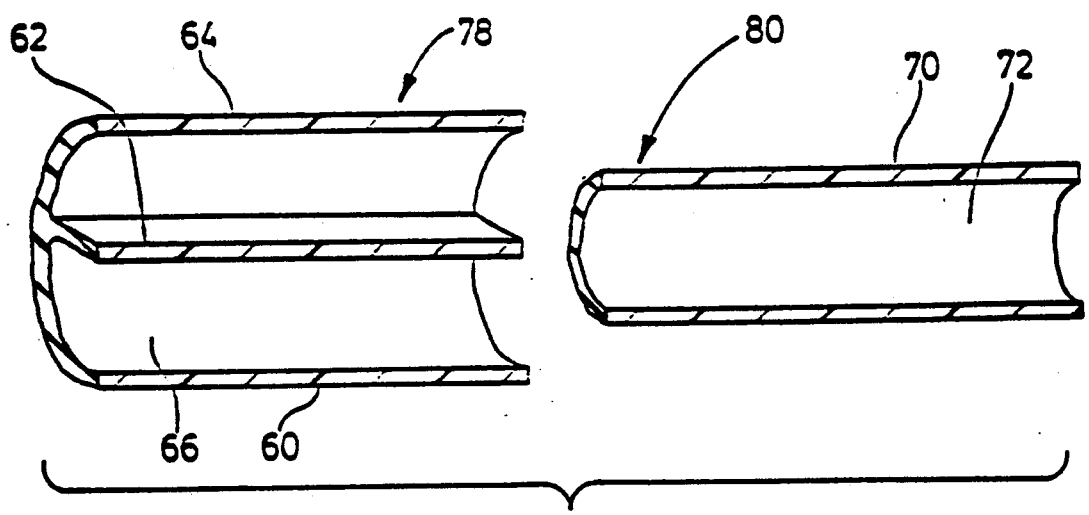
FIG. 8 is an enlarged sectional view of the distal end of a first portion and a second portion used to form the catheter of FIG. 1.

The shapes of extruded material used to make the catheter are shown in FIG. 8. Two lengths of smooth polyurethane tubing 78, 80 are used, the larger diameter tubing 78 being used to form the first portion 56, (FIG. 3) and the smaller diameter tubing 80 being used to form the second portion 58. Typically, the size of the larger tubing will be 11 French (11F) and the smaller tubing 8 French (8F). The larger cross-section tubing 78 is shorter than the desired total length of the catheter 20 and has an outer wall 60 of about 0.015 inches thickness and a integral septum 62 of about 0.010 inches thickness. The smaller cross-section tubing 80 is considerably shorter and has an outer wall 70 of about 0.017 inches thickness to define a single lumen 72.

Figure 9:
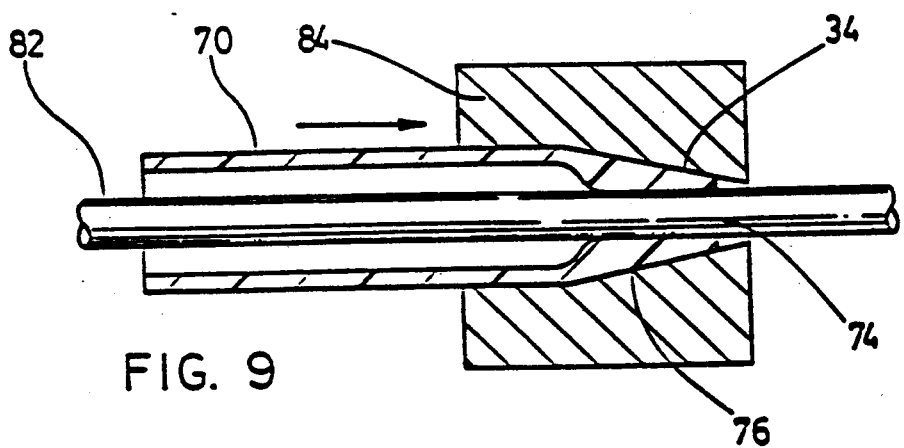

FIG. 9 illustrates the process used for forming the tip 34 on the smaller cross-section tubing 80. A round support wire 82 is placed inside a length of the tubing 80, which is then pushed into a heated die 84 having a shape corresponding to the desired shape of the portion 77 (FIG. 3). The wire 82 provides internal support during the forming operation. The tubing and wire are then removed from the die 84 and allowed to cool so that the tubing will harden.

Figure 10:
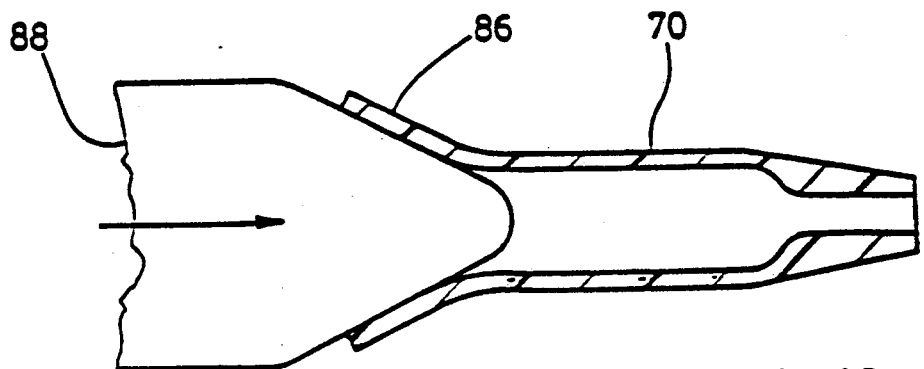

As shown in FIG. 10, a flared portion 86 is then formed on the other end of the tubing 80 by the insertion of a heated conical mandrel 88. The internal diameter of at least a part of the flared portion 86 is greater than the external diameter of the larger tubing 78. Thus, the smaller tubing 80 may be fitted over the distal end of the larger tubing 78, as shown in FIG. 9. However, before doing this, stiff support wires 94, 96 are located in the larger tubing 78, as shown in FIG. 11. The support wire 94 located in the passageway 64 has a D-shaped cross-section, as can be seen in FIG. 12, and a rounded end 97 which is located at the end of the passageway 64. The support wire 96 in the other passageway 66 has a portion 98 with a D-shaped cross-section, as seen in FIG. 12, which fits in the passageway 66 and an end portion 100 with a circular cross-section, as seen in FIG. 13, which extends from the end of the first portion 56. If reference is made to FIGS. 12 and 13, it will be noted that the cylindrical end portion 100 has a greater diameter than the height of the passageways in the dual lumen tubing seen in FIG. 12. It will be realised therefore that the walls and septum of the D-shaped passageway 66 must stretch to accommodate the cylindrical portion 100 on insertion and extraction of the wire 96. The support wires 94, 96 are then held in place and the flared portion 86 of the smaller tubing 80 pushed onto the distal end of the larger tubing, the cylindrical portion 100 of the support wire 96 being received by the tubing 80. It is important that the support wire 94, 96 do not touch to ensure that there is structural separation between the lumens after the catheter is completed.

Next, a silicon rubber sleeve 90 is slipped over the ends of the tubing 78, 80. The inner diameter of the sleeve 90 corresponds to the outer diameter of the original tubing 80 and tends to compress the ends of the tubing 78, 80 inwardly. To merge the tubing 78, 80, this assembly is located within two halves of a heated die 92 which is shown partially opened in FIG. 9.

Heat and pressure are applied by placing the heated die 92 in the sleeve 90, and the die 92 is held in place until the lengths of tubing 78, 80 are merged to form the portion 68 of gradually decreasing cross-section (FIG. 3) between the first and second portions 56, 58. After the tubing assembly is removed from the die 92, it is allowed to cool and harden before the sleeve 90 is removed. Next, the support wires 94, 96 are removed and the extraction and return apertures 52, 54 are formed by means of a trepaning tool (not shown). To locate the extraction aperture 52a at the end of the extraction lumen 64, a rod 102 of brightly coloured plastic material (FIG. 14) is inserted into the lumen 64 and pushed in until it will go no further. An operator looking at the catheter will then see the end of the rod 102 through the outer wall 60, and this end will show the termination of the lumen 64. The operator then forms the aperture 52a using the trepaning tool. The provision of the aperture 52a at this point avoids a dead space at the termination of lumen 64 where blood would otherwise stagnate.

Returning to FIG. 3 it will be seen that there is a thickening of material 101 in the outer wall at the transition portion 68, which helps to resist kinking at the point of change in cross-section, caused by bending and compression forces on the body 30 when the catheter is being inserted. It will also be seen that the outer surface of the portion 68 is smooth and that the change in cross-section is gradual.

The first portion 56 is supported against kinking and the aforementioned concertina effect during insertion by the Seldinger wire 22, and by the cylindrical form of the portion 56 which has considerable strength in compression.

It will of course be obvious to one skilled in the art that the steps above may be varied in sequence. For example, the flared portion 86 may be formed before the portion 77 of decreasing cross-section and this portion 77 may then be formed after the two pieces of tubing 78, 80 have been merged. In this case the support wire 96 is to be inserted from the distal end of the tubing 80 and similarly with the insertion of the support wire 96 described above, the tubing would have to stretch to accommodate the D-shaped portion as it is passed through the tubing 80.

If desired, the tubing 78, 80 may be of different colours to indicate the respective properties or diameters of the tubing and thus may serve to provide a clear indication to a physician of the properties of a particular catheter.

Figure 15:
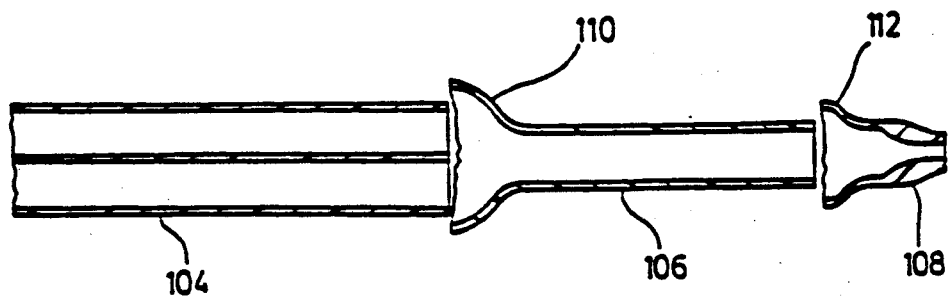
FIG. 15 is a sectional view illustrating the manufacture of a further embodiment of the catheter of the present invention.

FIG. 15 illustrates a step in the manufacture of a catheter in accordance with a further embodiment of the present invention. In this example the distal end of the catheter is being formed of three different pieces of tubing 104, 106, 108, the larger cross-section tubing 104 corresponding to the larger cross-section tubing 78, the smaller cross-section tubing 108 corresponding in cross-section to the smaller piece of tubing 80 though being considerably shorter, and an intermediate piece of tubing 106 of similar cross-section but of greater length than the tubing 108. The intermediate piece of tubing 106 is flared by a mandrel similar to that shown in FIG. 10 such that its flared portion 110 has an internal diameter greater than the external diameter of the tubing 104. The undeformed distal end of the tubing 106 is received by a flared portion 112 of the tubing 108. This embodiment illustrates that a greater number of pieces of tubing having differing properties may be used to form the distal end of a catheter having a combination of particular properties, and that a tip may be formed by different material having different properties. The tubing 108 would normally be of a softer or more flexible material to form a softer or more flexible tip.

Figure 16:
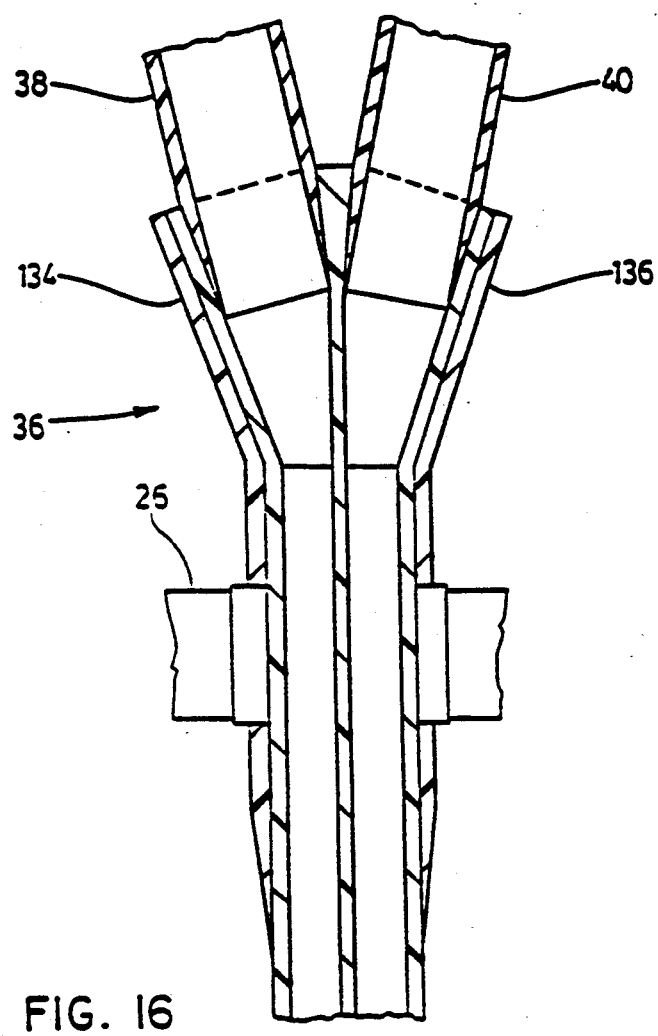
FIG. 16 is a sectional view of a Y-shaped branching connector seen at the proximal end of the catheter in FIG. 2 and drawn to a larger scale.

The method of manufacture of the Y-shaped branching connector 36 and reinforcing portion 50 will next be described with reference to FIGS. 16-21. The finished connector 36 is shown in FIG. 16 and the remaining figures are arranged in order of the manufacturing steps. It will be seen in FIG. 17 that the first portion 56 of the body 30 has received a short sleeve 114 of polyurethane, preferably the same colour as that used for the body. The sleeve 114 is a snug fit on the body 30 and after positioning on the body, the assembly is move into a heated mould 116 which has a conical interior wall 118 designed to deform the sleeve 114 to create a blended reinforcing portion 50 as shown in FIG. 2. If preferred, suitable support wires can be placed inside the passageways 64, 66 in the body 30 to avoid deforming passageways while the sleeve 114 is shaped in the mould 116.

The upper edge of the sleeve 114 (as drawn) is formed and is positioned for engagement with the attachment fitting 26 shown in FIG. 2 to locate this fitting longitudinally on the body.

After completing the process illustrated in FIG. 17, the fitting 26 is slipped over the end of the body 30 and into engagement with the sleeve 114. The fitting 26 is a loose fit so that it can rotate freely on the body 30. The positioning can be seen in FIG. 18 which also shows the completed reinforcing portion 50 and how it bends into the body 30.

Figure 19:
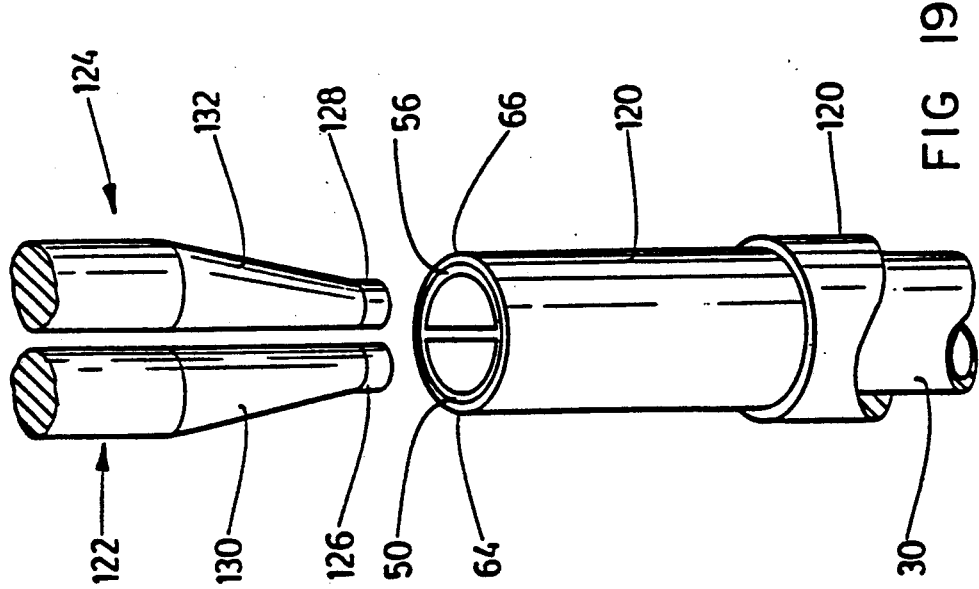

Next, another sleeve 120 (FIG. 18) is engaged over the end of the body 30 and, if the first sleeve has been positioned correctly, the sleeve 120 will be positioned so that its trailing edge is flush with the end of the body 30 as shown in FIG. 19. The sleeve 120 should not be pushed tightly against the attachment 26 in order to provide clearance for free movement of the fitting. With the sleeve in position, a pair of deforming mandrels are brought into play as seen in FIG. 19. There are two mandrels 122 and 124, one for each of the lumens, the mandrels being mirror images of one another. The intent of the mandrel is to form the corresponding passageways to have conical outer portions for receiving shaped ends of the tubes 38, 40 (FIG. 2) as shown in the completed connector 36 of FIG. 16.

The mandrels 122, 124 have respective leading ends 126, 128 which are proportioned simply to provide location as they enter the corresponding passageways 64, 66. The leading ends 126, 128 blend into respective conical portions 130, 132 which are arranged to complement one another so that the conical outer portions will flare outwardly to receive the tubes. Of course for simplicity of engagement purposes each of the mandrels is supported from shanks so that the mandrel can be brought into the extrusion longitudinally and deformation will take place because the conical portions are larger than the passageways and the material around the passageways will be forced outwardly under the influence of heat, by heating the mandrels. The extrusion itself is insufficient to support this increase size and retain sufficient strength, and this is why the second sleeve 120 is used.

Figure 21:
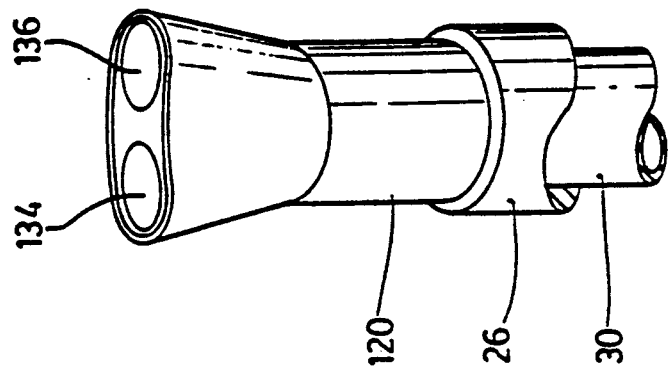
Figure 20:
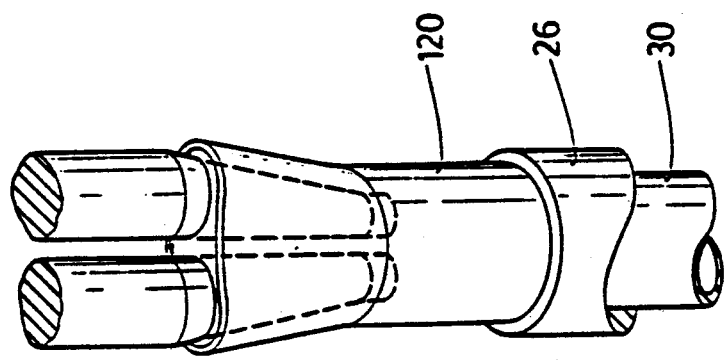

It will be seen in FIG. 20, that after the mandrels are engaged, the sleeve and contained portion of the extrusion are expanded, and after completion the appearance will be as shown in FIG. 21.

Reference is again made to FIG. 16, which shows the engagement of the tubes 38, 40 in the connector 36. These tubes have their engagement ends deformed to thin the wall and this is done by conical deformations so that the outer surface of the tubes are slightly conical to engage the corresponding internal cones 134, 136 shown in FIG. 21 and formed by the use of the mandrels. It will be seen in FIG. 16, that the resulting and assembly is compact, and provides a relatively smooth internal surface to minimize traumatic flow created forces on the blood as blood flow passes through the tubes and associated lumens. The tubes are attached in the connector 36 using support wires, a silicone sleeve, and a heated die, such that the material of the tubes and connector are merged together.

Obviously, the connector 36 may be formed in a number of ways, for example, in the reverse order to that described above. In this method the flares in the proximal end of the passageways 64, 66 are formed first, the fitting 26 then being slid over the distal end of the first portion before forming the reinforcing portion 50.

Thus, the catheters described above demonstrate embodiments of the present invention which facilitate insertion of a catheter through a skin puncture, while providing a flexible distal end portion or tip.

It will be clear to those skilled in the art that the embodiments described above are examples of the invention and that various modifications may be made to these within the scope of the present invention. For example, the catheters are described as being formed of polyurethane and it is clear that other materials having suitable properties may also be used.

I claim:

1. A dual lumen catheter for use in a vein to remove blood and to return treated blood to the vein comprising:

a flexible elongate body having first and second portions;

the first portion having a first cross-sectional area, a distal end, a proximal end, an outer wall and a continuous septum extending internally between spaced points on the outer wall to define D-shaped first and second passageways;

the second portion being tubular and having a second cross-sectional area smaller than said first cross-sectional area, a distal end with a cross-sectional area that reduces gradually to form a tip having an end opening, a proximal end, and an outer wall;

the distal end of the first portion being merged smoothly with the proximal end of the second portion at a transition portion which converges in cross-section from the first portion to the second portion;

the first passageway being closed at the transition portion to form a first lumen having a distal end at the transition portion;

at least one intake aperture at the distal end of the first lumen in the outer wall of the first portion providing access for blood into the first lumen;

the second passageway meeting the tubular portion at the transition portion to form a second lumen which terminates at said end opening to permit treated blood to be returned to the vein, and the second portion defining at least one blood return aperture in the same side of the catheter as the intake aperture and adjacent said end opening; and means coupled to the proximal end of the first portion to draw through the blood intake aperture and receive blood through the first lumen, and to return treated blood to the second lumen for flow into the vein through the blood return aperture and through the end opening.

2. A dual lumen catheter as claimed in claim 1, in which the second portion is more flexible than the first portion.

3. A dual lumen catheter as claimed in claim 1, in which the first and second portions are of different Durometer.

4. A catheter as claimed in claim 1, in which the first and second portions are formed of polyurethane having different physical properties, the material of the second portion having greater flexibility than the material of the first portion.

5. A dual lumen catheter for use in a vein to remove blood and to return treated blood to the vein comprising:
- a flexible elongate body having first and second portions;
- the first portion having a first cross-sectional area, a distal end, a proximal end, an outer wall and a continuous septum extending internally between spaced points on the outer wall to define D-shaped first and second passageways;
- the second portion being tubular and having a second cross-sectional area smaller than said first cross-sectional area, a distal end with a cross-sectional area that reduces gradually to form a tip having an end opening, a proximal end, and an outer wall;
- the distal end of the first portion being merged smoothly with the proximal end of the second portion at a transition portion which converges in cross-section from the first portion to the second portion;
- a thickening of material of the outer walls of the first and second portions at the transition portion;
- the first passageway gradually converging towards the transition portion and terminating at the transition portion to form a first lumen having a distal end at the transition portion;
- at least one intake aperture at the distal end of the first lumen in the outer wall of the first portion providing access for blood into the first lumen so that the blood may flow without stagnation;
- the second passageway meeting the tubular second portion at the transition portion to form a second lumen which terminates at said end opening to permit treated blood to be returned to the vein, the second passageway defining a blood return aperture in the same side of the catheter as the blood intake aperture and adjacent said end opening; and
- means coupled to the proximal end of the first portion to receive blood drawn through the blood intake aperture and through the first lumen, and to return treated blood to the second lumen for flow into the vein through the blood return aperture and through the end opening.

6. A dual lumen catheter as claimed in claim 5, in which the second portion is more flexible than the first portion.

7. A dual lumen catheter as claimed in claim 5, in which the first and second portions are of different Durometer.

8. A catheter as claimed in claim 5, in which the first and second portions are formed of polyurethane having different physical properties, the material of the second portion having greater flexibility than the material of the first portion.

* * * * *